US011013556B2

(12) United States Patent
Aeby

(10) Patent No.: US 11,013,556 B2
(45) Date of Patent: May 25, 2021

(54) CARDIAC CATHETER WITH DEFORMABLE BODY

(71) Applicant: St. Jude Medical, Cardiology Division, Inc., St. Paul, MN (US)

(72) Inventor: Nicolas Aeby, Geneva (CH)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 767 days.

(21) Appl. No.: 15/678,196

(22) Filed: Aug. 16, 2017

(65) Prior Publication Data

US 2018/0085158 A1 Mar. 29, 2018

Related U.S. Application Data

(60) Provisional application No. 62/399,684, filed on Sep. 26, 2016.

(51) Int. Cl.
*A61B 18/14* (2006.01)
*A61B 18/00* (2006.01)
*A61B 18/12* (2006.01)
*A61B 17/00* (2006.01)
*A61B 90/00* (2016.01)

(52) U.S. Cl.
CPC ...... *A61B 18/1492* (2013.01); *A61B 18/1206* (2013.01); *A61B 2017/00106* (2013.01); *A61B 2018/00023* (2013.01); *A61B 2018/00351* (2013.01); *A61B 2018/00577* (2013.01); *A61B 2018/00678* (2013.01); *A61B 2018/00839* (2013.01); *A61B 2018/00863* (2013.01); *A61B 2018/00988* (2013.01); *A61B 2018/1266* (2013.01); *A61B 2090/064* (2016.02); *A61B 2090/065* (2016.02); *A61B 2218/002* (2013.01)

(58) Field of Classification Search
CPC ............ A61B 18/1492; A61B 18/1233; A61B 18/1206; A61B 2018/00023; A61B 2018/1465; A61B 2018/1472; A61B 2018/00577; A61B 2018/00636; A61B 2018/00642; A61B 2018/00678; A61B 2018/00988; A61B 2018/00351; A61B 2018/00357; A61B 2017/00106; A61B 2090/064; A61B 2090/065
USPC ...... 606/34, 41, 42, 47, 49; 607/98, 99, 104, 607/105, 113, 115, 116, 122, 123
See application file for complete search history.

(56) References Cited

U.S. PATENT DOCUMENTS

| 7,662,151 | B2* | 2/2010 | Crompton, Jr. | ........ | A61B 18/14 |
| | | | | | 606/41 |
| 9,039,700 | B2* | 5/2015 | Kirschenman | ..... | A61B 18/1492 |
| | | | | | 606/41 |

(Continued)

FOREIGN PATENT DOCUMENTS

WO 2011033421 A1 3/2011

*Primary Examiner* — Thomas A Giuliani
(74) *Attorney, Agent, or Firm* — Dykema Gossett PLLC

(57) ABSTRACT

Aspects of the instant disclosure relate to an electrophysiological catheter system for performing diagnostics and therapies within a cardiac muscle; more specifically, to a deformable body, at a distal end of a catheter, that deforms in response to a force being exerted upon a tip of the catheter. The deformation of the deformable body being measured by a measurement device, and the deformation associated with both a magnitude and vector of the force exerted upon the catheter tip.

19 Claims, 9 Drawing Sheets

(56) References Cited

U.S. PATENT DOCUMENTS

2014/0187905 A1* 7/2014 Olson .................... A61B 5/066
600/409
2014/0276006 A1* 9/2014 Sliwa ................. A61B 18/1492
600/424

* cited by examiner

CARDIAC CATHETER WITH DEFORMABLE BODY

CROSS-REFERENCE TO RELATED APPLICATIONS

This application claims the benefit of U.S. provisional application No. 62/399,684, filed 26 Sep. 2016, which is hereby incorporated by reference as though fully set forth herein.

BACKGROUND a. Field

The instant disclosure relates to catheters, in particular catheters for conducting ablation therapy within tissue. In one embodiment, the instant disclosure relates to catheters for treating cardiac arrhythmias by ablating in the vicinity of pulmonary venous tissue.

b. Background Art

The human heart routinely experiences electrical impulses traversing its many surfaces and ventricles, including the left atrium. Just prior to each heart contraction, the heart depolarizes and repolarizes as electrical currents spread across the heart and throughout the body. In healthy hearts, the surfaces and ventricles of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to diagnose and correct conditions such as atrial arrhythmia, including for example, ectopic atrial tachycardia, atrial fibrillation, and atrial flutter. Typically, in such a procedure, a catheter is manipulated through a patient's vasculature to the patient's heart carrying one or more electrodes which may be used for mapping, ablation, diagnosis, or other treatment. Where an ablation therapy is desired to alleviate symptoms including atrial arrhythmia, the ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio-frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess force between the ablation catheter tip and the targeted myocardial tissue may result in excessive ablation which may permanently damage the cardiac muscle and/or surrounding nerves. When contact force between the ablation catheter tip and the targeted myocardial tissue is below a target force, the efficacy of the ablation therapy may be reduced.

Ablation therapies are often delivered by making a number of individual ablations in a controlled fashion in order to form a lesion line. To improve conformity of the individual ablations along the lesion line, it is desirable to precisely control the position at which the individual ablations are conducted, the ablation period, and the contact force between the ablation catheter tip and the targeted tissue. All of these factors affect the conformity of the resulting lesion line. Catheter localization systems, in conjunction with mapping systems, have vastly improved a clinician's ability to precisely position the ablation catheter tip for an ablation. Similarly, ablation controller circuitry has improved the consistency of individual ablation therapy. There are devices in development or being commercialized that attempt to measure the force exerted between myocardial tissue and the ablation catheter tip. Many existing designs utilize ablation catheter tips with deformable bodies which deform in response to a force being exerted on the ablation catheter tip. Sensors (e.g., magnetic, optical, interferometry, etc.) are used to approximate the deformation of the deformable body and to output a signal to controller circuitry that associates the deformation with a force exerted by the ablation catheter tip. However, existing deformable body designs suffer from complexity, cost, and the inability to distinguish between, and measure simultaneously, trans-axial and axial forces exerted on the ablation catheter tip. As a result, the calculated exerted force has a high error rate and the error rate greatly varies depending on the directionality at which the force is exerted upon the ablation catheter tip.

The foregoing discussion is intended only to illustrate the present field and should not be taken as a disavowal of claim scope.

BRIEF SUMMARY

The instant disclosure relates to catheters, in particular catheters for conducting tissue ablation therapy within tissue. More specifically, the instant disclosure relates to an ablation catheter with a deformable body that deforms in response to a force being exerted upon the ablation catheter tip.

In one exemplary embodiment of the present disclosure, an electrophysiological catheter system is disclosed. The electrophysiological catheter including a catheter shaft, a catheter tip, an elongated shaft, a deformable body, and one or more measurement devices. The catheter tip is coupled to a distal end of the catheter shaft, and conducts diagnostics and/or therapies on a cardiac muscle of a patient. The elongated shaft extends a length of the catheter shaft. The deformable body is coupled to the elongated shaft, and deforms in response to a force being translated from the catheter tip, through the elongated shaft, to the deformable body. Directionality of the exerted force on the catheter tip is discernible from the resulting deformation of the deformable body. The one or more measurement devices measure the resulting deformation of the deformable body in response to the force exerted on the catheter tip. The deformation of the deformable body is associated with a magnitude and vector of the force exerted on the catheter tip. In further more specific embodiments of the present disclosure, the deformable body includes one or more flexible disks that deform in response to the forces exerted on the catheter tip and translated to the deformable body. In such an embodiment, the resulting deformation of the one or more flexible disks is associated with the forces exerted on the catheter tip.

In another embodiment, an electrophysiology ablation catheter is disclosed including a catheter tip, a catheter shaft, an elongated shaft that extends along a length of the catheter shaft, a deformable body, a measurement device, and a force sensing subsystem. The catheter tip is coupled to a distal end of the catheter shaft, and conducts diagnostics or therapies on a cardiac muscle. The deformable body is coupled to the elongated shaft, and deforms in response to a force being translated from the catheter tip, through the elongated shaft, to the deformable body. In such an embodiment, a magnitude and vector of the exerted force on the catheter tip is discernible from the resulting deformation of the deformable body. The measurement device measures the resulting deformation of the deformable body in response to the force exerted on the catheter tip, and the force sensing subsystem derives the magnitude and vector of the force exerted on the catheter tip based on the deformation measurements of the measurement device.

In yet other embodiments, an electrophysiology ablation catheter system is disclosed including an ablation catheter tip that conducts ablation therapy on a cardiac muscle, a catheter shaft, an elongated shaft that extends the length of the catheter shaft, a deformable body, and three or more ultrasonic transducers. The deformable body is coupled to a proximal end of the ablation catheter tip and a distal end of the catheter body via the elongated shaft. The deformable body includes one or more flexible disks that couple the ablation catheter tip to the catheter shaft, and deforms in response to a force being translated from the catheter tip, through the elongated shaft, to the deformable body. The three or more ultrasonic transducers, in response to the force exerted on the ablation catheter tip, measure the resulting deformation at three or more points of the deformable body. The deformation of the deformable body, as measured by the three or more ultrasonic transducers, being indicative of both the magnitude and vector of the force exerted on the ablation catheter tip.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
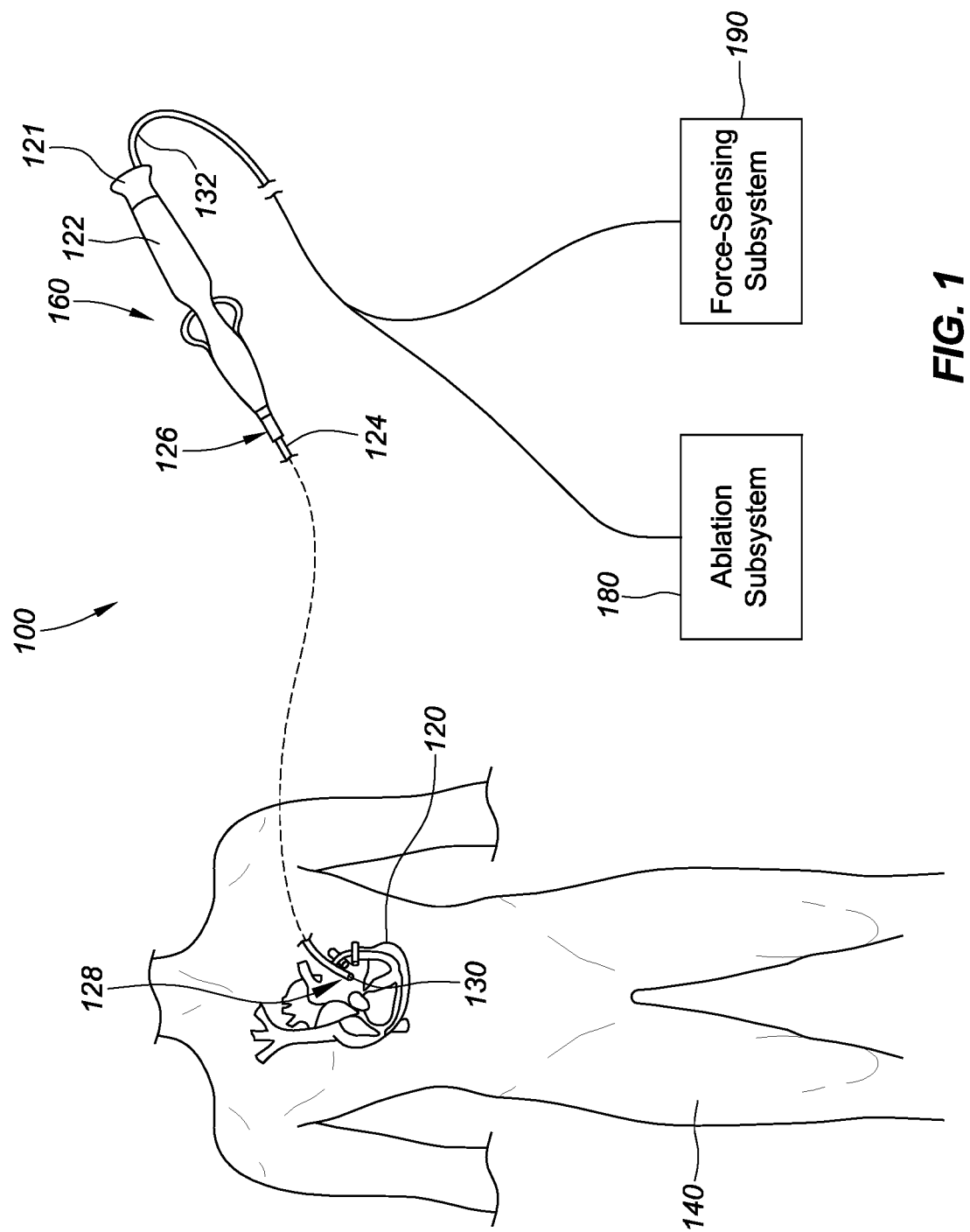
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for tissue ablation within tissue. More specifically, the instant disclosure relates to an ablation catheter including a deformable body that deforms in response to a force exerted on a tip of the catheter. Details of the various embodiments of the present disclosure are described below with specific reference to the figures.

Referring now to the drawings wherein like reference numerals are used to identify similar components in the various views, FIG. 1 is a schematic and diagrammatic view of an electrophysiological catheter system 100 for performing diagnostics and therapies within a cardiac muscle of a human body 140, for example, ablation therapy of tissue 120. It should be understood, however, that catheter systems consistent with aspects of the present disclosure may find application in connection with a variety of other locations within human and non-human bodies, and therefore, the present disclosure is not meant to be limited to the use of the system in connection with only cardiac tissue and/or human bodies, or in regard to ablation therapies.

Electrophysiological catheter system 100 may include a catheter 160, an ablation subsystem 180 for controlling an ablation therapy conducted by an ablation catheter tip 130 at a distal end of the catheter. The ablation subsystem may control the application of and/or generation of ablative energy including, for example, radio frequency (RF), cryoablation, laser, chemical, and high-intensity focused ultrasound, among others. The catheter system may further include a force-sensing subsystem 190 for determining and indicating to a clinician when the ablation catheter tip comes in contact with myocardial tissue within the cardiac muscle (among other impediments), and how much pressure is exerted upon the myocardial tissue by the ablation catheter tip. Ablation therapies often require precise force exertion for optimal ablative-energy transfer into the targeted myocardial tissue. Excess force between the ablation catheter tip and the targeted myocardial tissue may result in excessive ablation which may permanently damage the cardiac muscle and/or surrounding nerves. In contrast, contact force below a target force between the ablation catheter tip and the targeted myocardial tissue may reduce the efficacy of the ablation therapy, as insufficient ablative energy is transferred to the myocardial tissue. In such a case, myocardial tissue receiving the ablative therapy may regenerate and continue conducting electrical impulses.

In the exemplary embodiment of FIG. 1, catheter 160 is provided for examination, diagnosis, and/or treatment of internal body tissue such as cardiac tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation catheter tip 130 coupled to the distal end of the catheter shaft. In many embodiments, the handle may include inputs for a clinician to control the function of catheter tip (e.g., ablation) and/or exert steering inputs for the catheter shaft.

In an exemplary embodiment, ablation catheter tip 130 is manipulated through vasculature of a patient 140 using handle 122 to steer one or more portions of shaft 124 and position the ablation catheter tip at a desired location within heart 120. In various embodiments, the ablation catheter tip includes ablation elements (e.g., ablation electrodes, high intensity focused ultrasonic ablation elements, etc.) that when operated by ablation subsystem 180 ablates the tissue in contact with the ablation catheter tip (and in some cases tissue in proximity to the ablation catheter tip may be ablated by conductive energy transfer through the blood pool and to the proximal tissue). To verify that proper contact is maintained during the ablation therapy, the deformation of a deformable body within the ablation catheter tip is measured and an output is sent to force-sensing subsystem 190. The force-sensing subsystem associates the deformation of the deformable body with a force exerted on the myocardial tissue being ablated, and may display the calculated force for the clinician or otherwise intervene during the ablation therapy where necessary to maintain the efficacy of the therapy.

In various specific embodiments of the present disclosure, catheter 160 may include electrodes and one or more positioning sensors at a distal end 128 of catheter shaft 124 (e.g., electrodes or magnetic sensors). In such an embodiment, the electrodes acquire electrophysiology data (also referred to as "EP data") relating to cardiac tissue within heart 120, while the positioning sensor(s) generate positioning data indicative of the 3-D position of the ablation catheter tip 130. In further embodiments, the catheter may include other conventional catheter components such as, for example and without limitation, steering wires and actuators, irrigation lumens and ports, pressure sensors, contact sensors, temperature sensors, additional electrodes, and corresponding conductors or leads.

Connector 121 provides mechanical and electrical connection(s) for one or more cables 132 extending, for example, from ablation subsystem 180 to ablation catheter tip 130 mounted on distal end 128 of catheter shaft 124. In other embodiments, the connector may also provide mechanical, electrical, and/or fluid connections for cables extending from other components in catheter system 100, such as, for example, a fluid source (when the catheter 160 includes an irrigated catheter tip) and force-sensing subsystem 190 (when the catheter tip includes a deformable body for measuring force exerted by the catheter tip on myocardial tissue in contact therewith). In reference to measuring a force exerted by the catheter tip, the ultrasonic transducer (by way of example) may require the force-sensing subsystem to conduct back-end processing of an output signal of the ultrasonic transducer. The connector is conventional in the art and is disposed at a proximal end 126 of catheter 160.

Handle 122 provides a location for a clinician to operate catheter 160 and may further provide steering or guidance inputs for catheter shaft 124 while inserted within a patient's body 140. For example, the handle may include means to manipulate one or more steering wires extending through the catheter to a distal end 128 of the shaft to steer the shaft. The handle is conventional in the art and it will be understood that the construction of the handle may vary. In other embodiments, control of the catheter may be automated by robotically driving or controlling the catheter shaft, or driving and controlling the catheter shaft using a magnetic-based guidance system.

Catheter shaft 124 is an elongated, tubular, and flexible member configured for movement within a patient's body 140. The shaft supports an ablation catheter tip 130 at a distal end 128 of catheter 160. The shaft may also permit transport, delivery and/or removal of fluids (including irrigation fluids, cryogenic ablation fluids, and body fluids), medicines, and/or surgical tools or instruments. The shaft, which may be made from conventional materials used for catheters, such as polyurethane, defines one or more lumens configured to house and/or transport electrical conductors, fluids, surgical tools, and/or steering cables. The catheter may be introduced into a blood vessel or other structure within the body through a conventional introducer sheath.

In an exemplary cardiac ablation therapy, to correct for atrial arrhythmia, the introducer sheath is introduced through a peripheral vein (typically a femoral vein) and advanced into a right atrium of a patient's cardiac muscle 120, in what is referred to as a transeptal approach. The introducer sheath then makes an incision in the fossa ovalis (the tissue wall between the left and right atriums), and extends through the incision in the fossa ovalis to anchor the introducer sheath in the fossa ovalis. The ablation catheter 160 may then be extended through a lumen of the introducer sheath into the left atrium. Catheter shaft 124 may then be steered or guided through the left atrium to position an ablation catheter tip 130 into a desired location within the left atrium such as in proximity to a pulmonary vein where an ablation therapy is to be applied.

Aspects of the present disclosure improve the efficacy of ablation therapy by more effectively maintaining a consistent force between ablation catheter tip 130 and myocardial tissue being ablated during a single-point ablation, as well as along a lesion line comprising a number of individual ablations. In more specific embodiments, the ablation catheter tip further improves ablation therapy efficacy by having improved force exertion sensing accuracy regardless of the contact location of the myocardial tissue on the ablation catheter tip. Accordingly, the accuracy of the sensed force on the ablation catheter tip is consistent whether the force is exerted axially or trans-axially relative to the catheter shaft.

Figure 2:
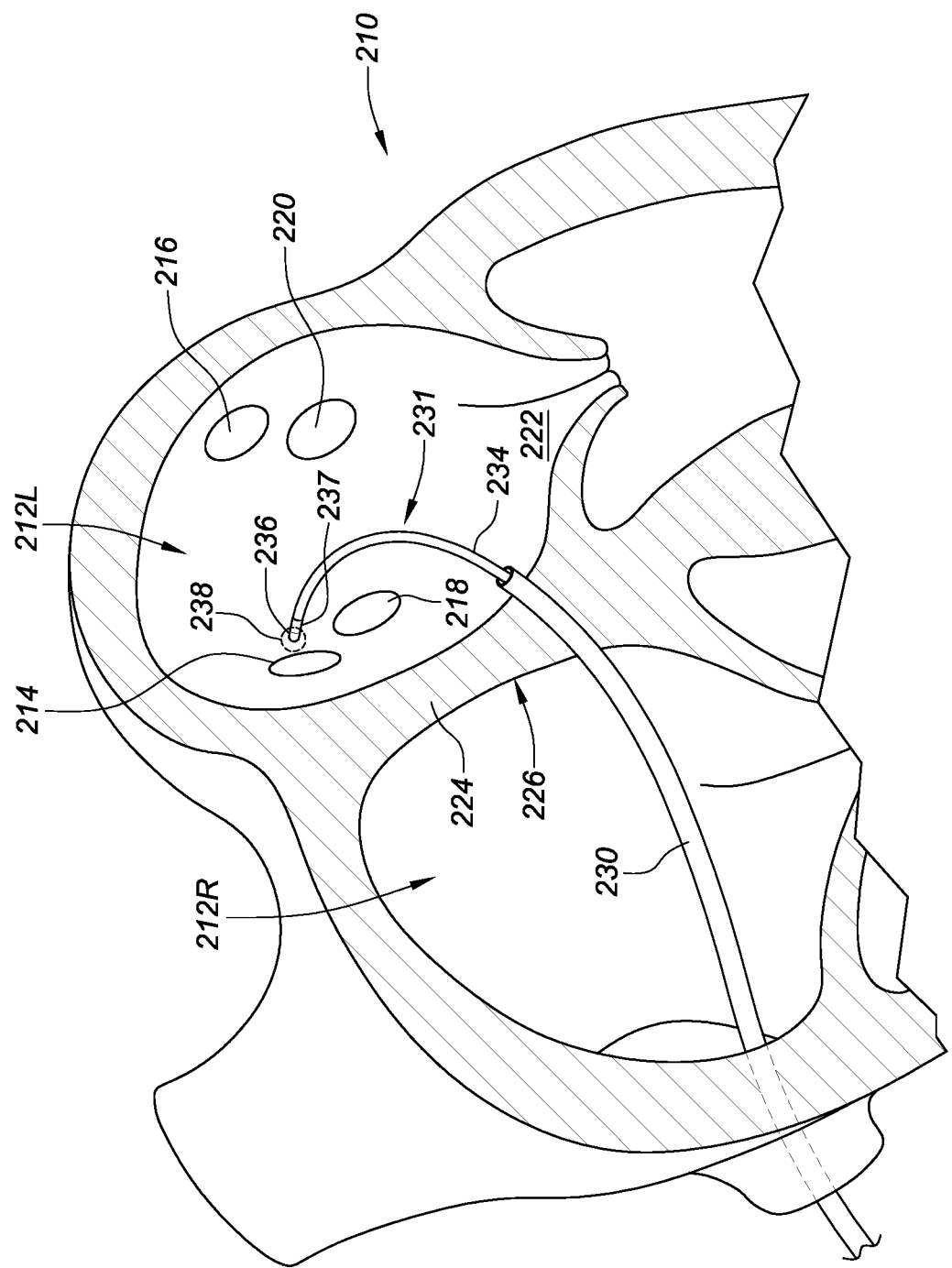
FIG. 2 is a cross-sectional view of a left atrium of a cardiac muscle with an ablation catheter extending into contact with an antrum of a pulmonary vein, consistent with various aspects of the present disclosure.

FIG. 2 is a cross-sectional front-view of a portion of cardiac muscle 210 with an ablation catheter 231 locating a pulmonary vein (e.g., 214, 216, 218, and 220) for performing atrial fibrillation therapy, consistent with various aspects of the present disclosure. As shown in FIG. 2, the cardiac muscle 210 includes two upper chambers called the left atrium 212L and right atrium 212R, and two lower chambers called the left ventricle and right ventricle (not shown).

Aspects of the present disclosure are directed to ablation therapies in which tissue in pulmonary veins 214, 216, 218, and 220, which form conductive pathways for electrical signals traveling through the tissue, is destroyed in order to electrically isolate sources of unwanted electrical impulses (arrhythmiatic foci) located in the pulmonary veins. By either destroying the arrhythmiatic foci, or electrically isolating them from the left atrium 212L, the cause of atrial fibrillation can be reduced or eliminated.

As shown in FIG. 2, an ablation catheter 231 may be introduced into the left atrium 212L by an introducer sheath 230. A catheter shaft 234 may guide the ablation catheter tip 236 once introduced into the left atrium by the introducer sheath. Optionally, the ablation catheter tip may include mapping electrodes to conduct electrophysiological diagnostics of the myocardial tissue within the left atrium. Specifically, myocardial tissue in proximity to one or more of the pulmonary veins 214, 216, 218, and 220. In operation, the introducer sheath has its distal end positioned within the left atrium. As shown in FIG. 2, a transeptal approach may be utilized in which introducer sheath is introduced through a peripheral vein (typically a femoral vein) and advanced to right atrium 212R. The introducer sheath makes a small incision into the fossa ovalis 226 which allows the distal end of the introducer sheath to enter the left atrium and to anchor itself to the wall 224 of the fossa ovalis.

Ablation catheter 231 may also be introduced into left atrium 212L through the arterial system. In that case, introducer sheath 230 is introduced into an artery (such as a femoral artery) and advanced retrograde through the artery to the aorta, the aortic arch, and into the left ventricle. The ablation catheter is then extended from within a lumen of the introducer sheath to enter the left atrium through mitral valve 222.

Once introducer sheath 230 is in position within left atrium 212L, steerable catheter shaft 234 is advanced out a distal end of the introducer sheath and toward one of the pulmonary veins (e.g., 214, 216, 218, and 220). In FIG. 2, the target pulmonary vein is right superior pulmonary vein 214. A steerable portion of the catheter shaft is manipulated until the distal tip of the ablation catheter tip 236 is directed toward the ostium of the target pulmonary vein.

Optionally, the embodiment of FIG. 2 may include mapping electrodes at a tip 236 of ablation catheter 231. The mapping electrodes may be ring electrodes that allow the clinician to perform a pre-ablation therapy electrical mapping of the conduction potentials of the pulmonary vein. Alternatively, the mapping electrodes may be carried on-board a separate electrophysiology catheter.

To ablate the tissue, once in contact with targeted tissue 238 of the pulmonary vein, ablation catheter tip 236 may electrically conduct a DC energy current into the targeted tissue of the pulmonary vein 214. In other embodiments, the ablation catheter tip may transmit radio-frequency energy to ablate the target tissue. In yet other embodiments, the ablation catheter tip may deliver one or more of the following energies to the targeted tissue: cryoablation, laser, chemical, and high-intensity focused ultrasound, among others. After a controlled therapy application, necrosis of the targeted tissue along a lesion line increases the resistance of the pulmonary vein to the flow of electrical signals through the pulmonary vein to the cardiac muscle.

During ablation therapy, contact force between target myocardial tissue 238 and ablation catheter tip 236 is translated through an elongated shaft, that forms an irrigant lumen, and that extends through the catheter to a deformable body 237 which absorbs the exerted force by deforming. Accordingly, the amount of deformation of the deformable body is associated with a force exerted on the myocardial tissue by the ablation catheter tip.

Ablation catheter tip 236 may ablate myocardial tissue using ablation electrodes that emit radiofrequency signals for ablating the tissue in proximity to the distal end of the ablation catheter tip. The ablation electrodes are controlled by controller circuitry, at a proximal end of the catheter shaft, that communicates with the ablation electrodes and transmits generated radiofrequency signals to the ablation electrodes via one or more lead wires which are housed within the catheter shaft 234. To prevent blood pooling around the distal end of the ablation catheter tip during ablation therapy, the ablation catheter tip may include irrigant ports that emit a saline solution around the distal end of the ablation catheter tip in proximity to the tissue being ablated. A fluid lumen housed within the catheter shaft provides a supply of saline solution to the irrigant ports from a reservoir at a proximal end of the catheter shaft.

In atrial fibrillation cases (among other arrhythmias), unwanted electrical impulses emanating from the pulmonary veins may enter the heart and cause irregular rhythms and rhythm rates. By either destroying arrhythmiatic foci (associated with the electrical impulses), or electrically isolating the foci from the left atrium, for example, atrial fibrillation can be reduced or eliminated. To the extent that arrhythmiatic foci are located within a tissue ablation zone, the arrhythmiatic foci are destroyed. To the extent the arrhythmiatic foci are located in a target pulmonary vein, on the opposite side of an ablation zone from the cardiac muscle, the electrical impulses produced by those foci are blocked or inhibited by the ablation zone.

During an exemplary ablation therapy, ablation catheter tip 236 contacts ablation targeted myocardial tissue 238 in order to conductively transfer radiofrequency energy from the ablation electrodes to the targeted myocardial tissue. It has been discovered that consistent force, during a series of tissue ablations, forms a more uniform lesion line. Such uniform lesion lines have been found to better isolate the electrical impulses produced by arrhytmiatic foci, thereby improving the overall efficacy of the ablation therapy. To achieve such consistent force, aspects of the present disclosure utilize a deformable body 237 in catheter 231. The deformable body deforms in response to the ablation catheter tip exerting a force upon the targeted myocardial tissue. The deformation of the deformable body may then be measured by a measurement device (e.g., ultrasonic, magnetic, optical, interferometry, etc.). The deformation may then be associated with a force exerted on the distal end of the ablation catheter tip (e.g., via a lookup table). The measurement device (in conjunction with controller circuitry, e.g., a force sensing subsystem) may then output a signal indicative of an external force exerted on the ablation catheter tip. The calculated force may then be displayed to the clinician or otherwise communicated. For example, haptic feedback may be utilized in the catheter handle to indicate proper or insufficient contact force with the targeted myocardial tissue.

As will be discussed in more detail below, aspects of deformable body 237 of the present disclosure allow one or more measurement devices to determine both a force magnitude and a vector exerted by ablation catheter tip 236 on myocardial tissue based upon the deformable body's deformation in response to an external force being exerted upon ablation catheter tip 236.

Figure 3A:
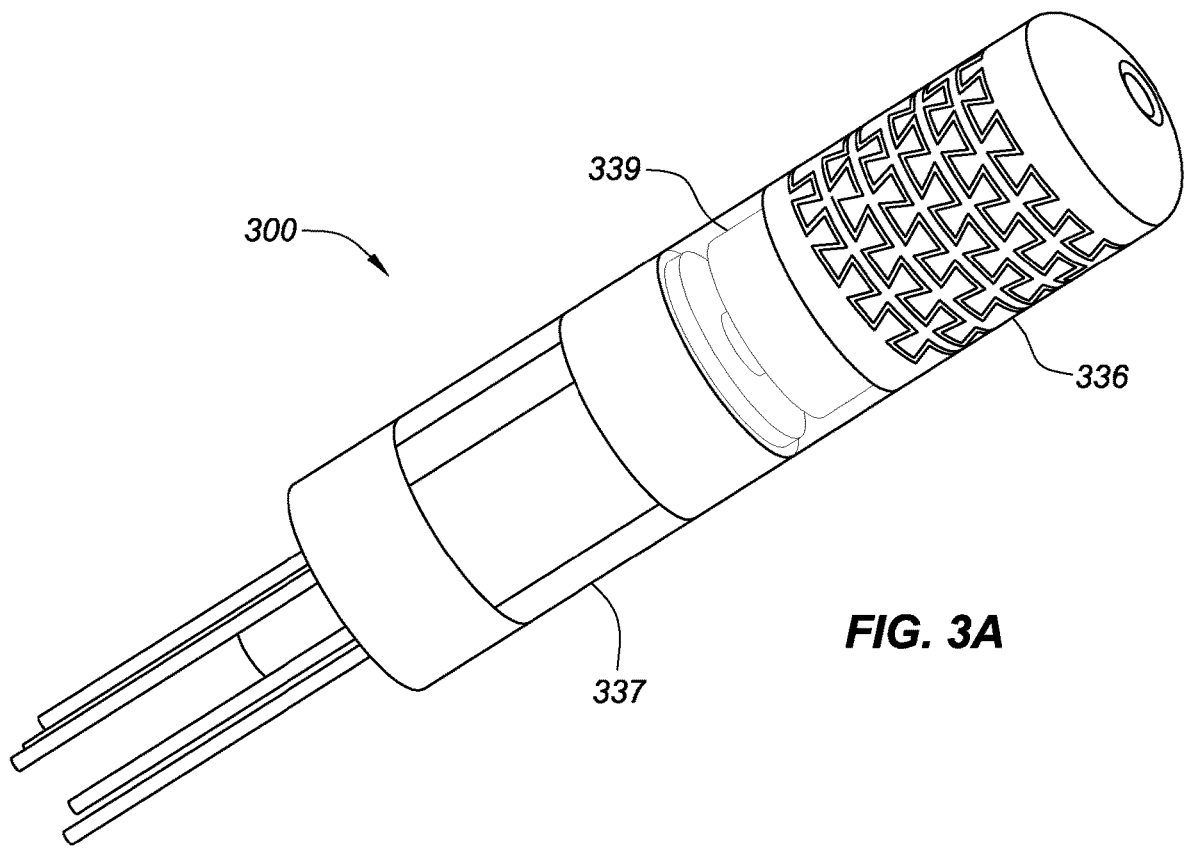
FIG. 3A is an isometric view of an ablation catheter tip subassembly, consistent with various aspects of the present disclosure.
Figure 3B:
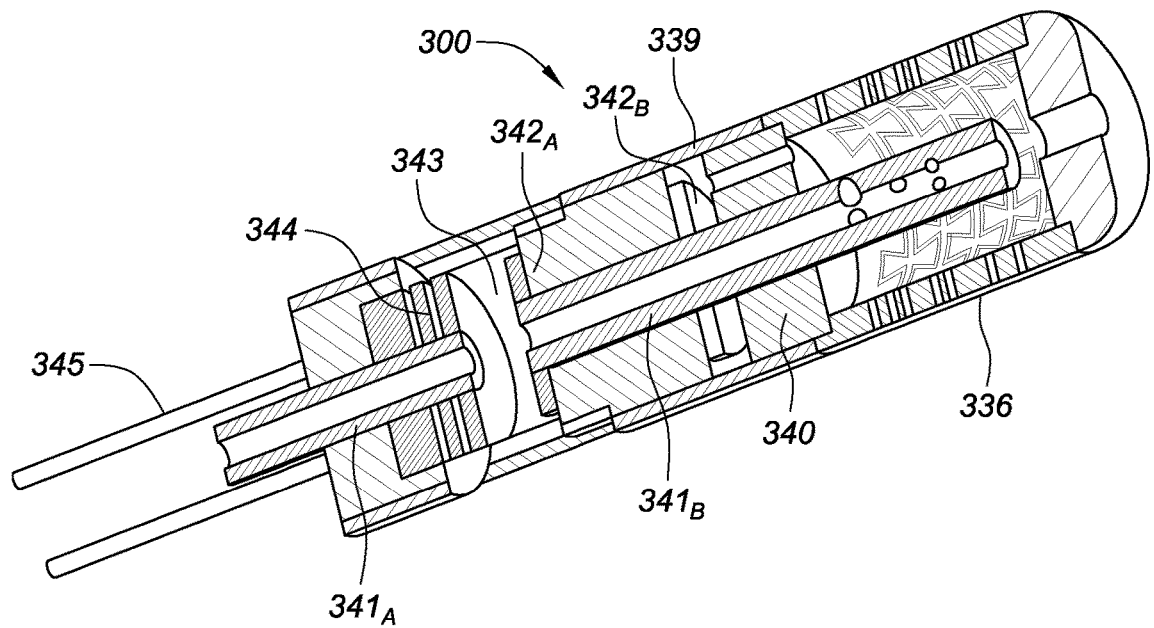
FIG. 3B is an cross-sectional isometric view of the ablation catheter tip subassembly of FIG. 3A, consistent with various aspects of the present disclosure.

FIGS. 3A and 3B show views of a catheter tip subassembly 300 including an ablation catheter tip 336 and deformable body 337 which are coupled to one another, with the joint between the two being sealed with a soft interface seal 339 (and interface 340, which in specific embodiments may consist of titanium), consistent with various aspects of the present disclosure. The subassembly 300 further includes portions of an elongated shaft $341_{A-B}$, that forms an irrigant lumen, and that substantially extends the length of the subassembly 300 and delivers an irrigant fluid to the ablation catheter tip 336 for cooling of the blood pool during ablation therapies within a cardiac muscle. As the soft interface seal 339 between the ablation catheter tip 336 and the deformable body 337 provides little structural support, the elongated shaft substantially supports the ablation catheter tip and transfers a force exerted on the ablation catheter tip into the deformable body.

A force received by ablation catheter tip 336 is translated by elongated shaft $341_B$ into deformable body 337. Disk $342_B$, within the deformable body 337, receives the force and deforms in response thereto. Disk $342_B$ is coupled to an exterior housing of the deformable body along an outer circumference of the disk, and the elongated shaft extends through (and couples to) a central axis of disks $342_{A-B}$.

During an ablation therapy of myocardial tissue within the heart, irrigant fluid flows through an irrigant lumen within elongated shaft $341_A$ which extends the length of the catheter shaft between a reservoir and an immersed zone 343. The immersed zone 343 fills with the irrigant fluid before the irrigant fluid extends through an irrigant lumen within elongated shaft $341_B$ to ablation catheter tip 336 where the fluid exits the ablation catheter tip through one or more ports. In the present embodiment, to achieve energy transfer between the ablation catheter tip and targeted myocardial tissue for the ablation therapy, the ablation catheter tip and myocardial tissue must come into contact with one another.

As discussed earlier, maintaining a force between the ablation catheter tip and the tissue is desirable for ablation consistency and efficacy. The contact force exerted on the tissue by the ablation catheter tip is translated through irrigant lumen within elongated shaft $341_B$ and into disk $342_B$ which deforms proportionally in response to the contact force exerted thereon. The deformation of disk $342_B$ changes the relative distance between disk $342_A$ and an ultrasonic probe 344. During the ablation therapy, ultrasonic probe 344 (including one or more ultrasonic transducers) measures the time-of-flight of an ultrasonic pulse (the time it takes for the ultrasonic pulse emitted by the ultrasonic probe to travel through immersed zone 343, reflect off of disk $342_A$ and travel back to the ultrasonic probe). The time-of-flight for the emitted ultrasonic pulse varies based on the magnitude and directionality of deformation of disk $342_B$. Back-end processing may then be utilized to calculate, based on the time-of-flight for the emitted ultrasonic pulse, the distance between disk $342_A$ and the ultrasonic probe. In further more specific embodiments, back-end processing associates the distance between the disk and the ultrasonic probe with the force exerted upon the ablation catheter tip resulting in the deformation of deformable body 337. An output signal from the ultrasonic probe may then communicate via lead wires 345 extending through the length of the catheter shaft for further processing, and/or communication with the clinician conducting the ablation therapy. As will be discussed in more detail below, aspects of the present disclosure determine both a magnitude and vector of a force exerted on ablation catheter tip 336 by measuring the displacement of at least disk $342_A$ at more than one location. When the measured deformations are associated time-wise with one another and compiled, the displacement along the entire surface of the disk may be accurately estimated, and an associated magnitude and vector of the force causing the deformation of disk $342_B$ may be determined.

Importantly, dimensional aspects of the disks may be tuned (e.g., thickness, diameters, and distance between the disks) in order to achieve desired compliance ratios related to the displacement of the deformable body in respect to axial and trans-axial forces exerted at a distal end of the inner shaft. In many applications, a trans-axial/axial compliance ratio of less than 5 may be desirable. The transaxial/axial compliance ratio is a comparison of the deformation of deformable body 339 in response to an axial force compared to a trans-axial force (with the same magnitude of the axial force). As an example, if the deformable body deforms 5 micrometers in response to a 1 Newton trans-axial force, and 1 micrometer in response to that same 1 Newton force exerted along the deformable body's axis, the transaxial/axial compliance ratio of such a deformable body is 5. Accordingly, embodiments consistent with the present disclosure may decrease a perpendicular load compliance of the deformable body without causing a concomitant decrease in the axial load compliance. As a result, the predictability of a force vector exerted on the ablation catheter tip may be more accurately estimated.

FIGS. 4A-4D show views of an ultrasonic transducer assembly 444 (in various stages of assembly), consistent with various aspects of the present disclosure. The ultrasonic transducer assembly includes an elongated shaft 441 that extends through an axis of the ultrasonic transducer assembly and structurally supports the rest of the assembly. Piezoelectric crystals 457 (coupled to solder pads 456) generate the ultrasonic impulses, and are electrically coupled to piezo electrode $452_A$ which supplies current to and excites the piezoelectric crystals via wires 445. A thickness of the piezoelectric crystals being controlled by $\lambda/2$ (where $\lambda$ is the transmitted ultrasonic wavelength).

Figure 4A:
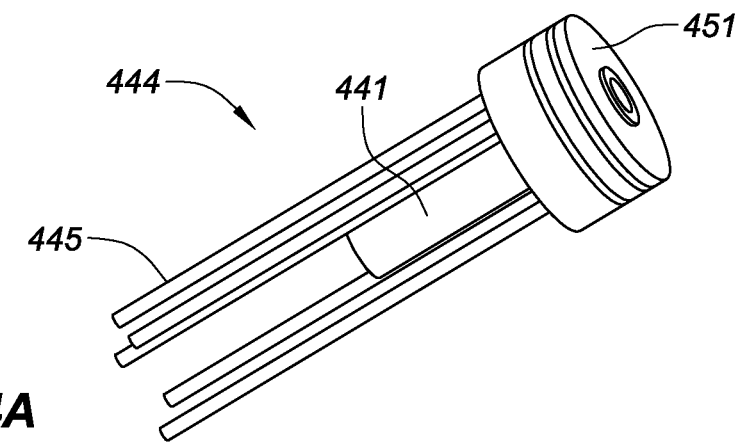
FIG. 4A is an isometric view of an ultrasonic transducer assembly, consistent with various aspects of the present disclosure.
Figure 4B:
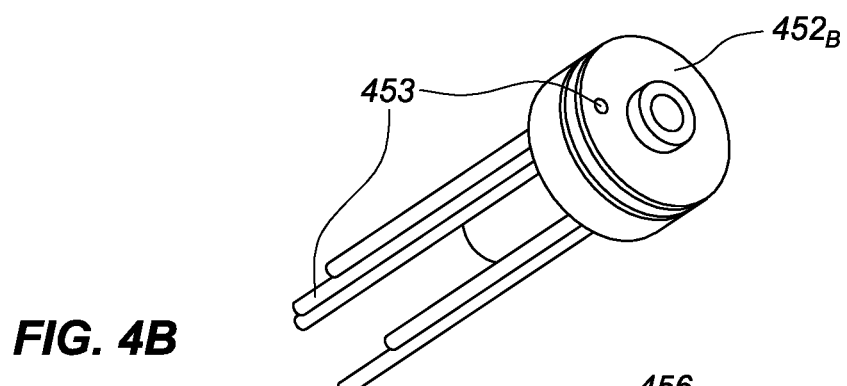
FIG. 4B is an isometric view of a partial ultrasonic transducer assembly, consistent with various aspects of the present disclosure.
Figure 4C:
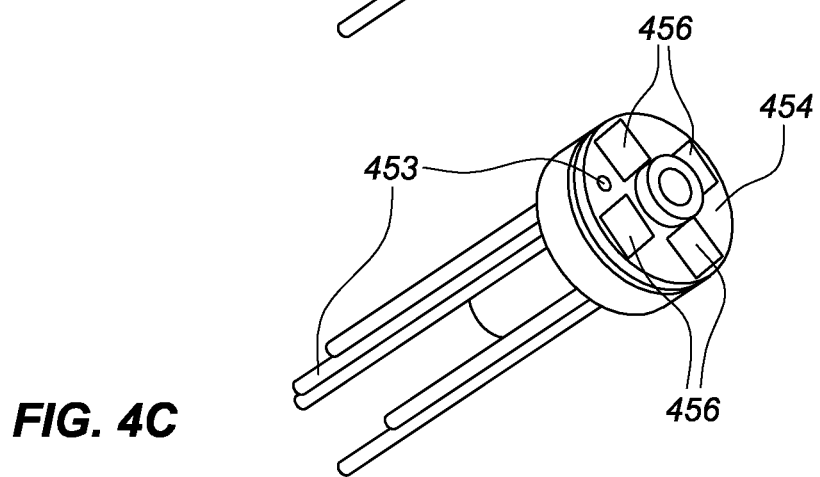
FIG. 4C is an isometric view of a partial ultrasonic transducer assembly, consistent with various aspects of the present disclosure.

As shown in FIG. 4C, solder pads 456 are placed onto a top surface of intermediate layer 454 (e.g., a polymer).

A backing layer 458 attenuates the ultrasonic impulses, and prevents the impulses from being reflected back on the ablation catheter tip subassembly. A ground wire 453 (among other wires), coupled to piezo electrode 452$_B$, extends through the various layers of the ultrasonic transducer assembly 444 and provides common ground to the other sides of the ultrasonic transducer assembly.

A matching layer 451 at a distal end of the ultrasonic transducer assembly optimizes the ultrasonic impulse emission. In various embodiments of the present disclosure, the matching layer may comprise a material optimized at the level of the acoustic impedance of the medium the ultrasonic impulse will be traveling through, and thereby optimized to mitigate acoustic loss. The thickness of the matching layer controlled by $\lambda/4$.

In further embodiments, ultrasonic transducers positioned at a fixed distance from a deformable body output a signal in response to the ultrasonic transducer transmitting an ultrasonic pulse, and not receiving a reflected ultrasonic pulse within a threshold time period. The output signal being indicative of an occlusion in the irrigant lumen, within the elongated shaft 441, that prevents the flow of irrigant fluid to the ablation catheter tip or presence of air bubbles, and acts as a safe guard against conducting ablation therapies without cooling the blood pool in proximity to the ablation catheter tip with the irrigant.

In some specific embodiments that are susceptible to low signal-to-noise ratios, controller circuitry (e.g., a force sensing subsystem, or the ultrasonic transducer itself) receiving the output signal from the ultrasonic transducer may ignore a variation in the output signal if the signal does not exceed a threshold indicative of external contact with the catheter tip.

Figure 5A:
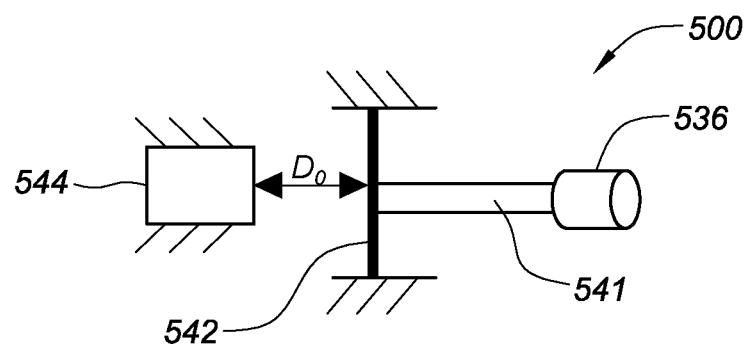
FIG. 5A is a side view of an ablation catheter tip subassembly, consistent with various aspects of the present disclosure.
Figure 5B:
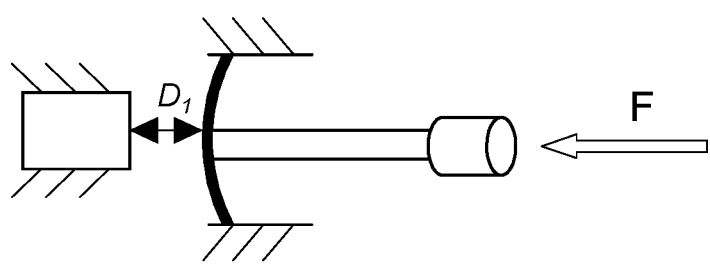
FIG. 5B is a side view of the ablation catheter tip subassembly of FIG. 5A, where the ablation catheter tip is under an axial compressive force, consistent with various aspects of the present disclosure.
Figure 5C:
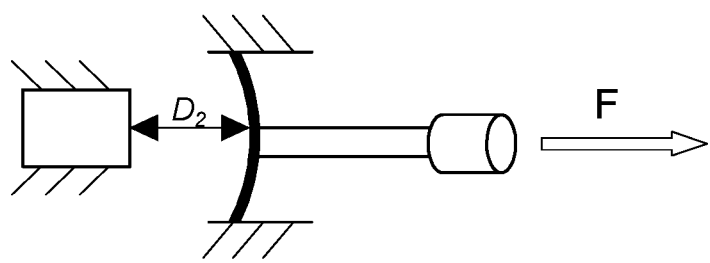
FIG. 5C is a side view of the ablation catheter tip subassembly of FIG. 5A, where the ablation catheter tip is under an axial tensile force, consistent with various aspects of the present disclosure.
Figure 5D:
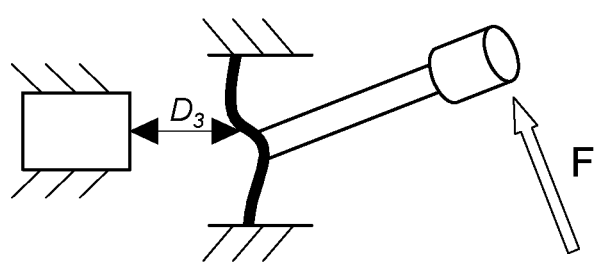
FIG. 5D is a side view of the ablation catheter tip subassembly of FIG. 5A, where the ablation catheter tip is under a trans-axial compressive force, consistent with various aspects of the present disclosure.

FIGS. 5A-5D show a simplified embodiment of an ablation catheter tip subassembly 500 including an ultrasonic transducer 544 that measures the deformation of a disk 542. The deformation of the disk being associated with a magnitude and vector of a force exerted on ablation catheter tip 536, and translated to the disk by elongated shaft 541. FIG. 5A shows the ablation catheter tip subassembly at a time $t_0$ (with no force being exerted on the ablation catheter tip). When at rest, the distance between the ultrasonic transducer and the disk is $D_0$. As shown in FIG. 5B, at time $t_1$ an axial compressive force is exerted on the ablation catheter tip resulting in a deformation of the disk toward the ultrasonic transducer. As a result of the axial compression force, the measured distance between the ultrasonic transducer and the disk is $D_1$, where $D_1 < D_0$. As shown in FIG. 5C, at time $t_2$ an axial tensile force is being exerted on the ablation catheter tip resulting in a deformation of the disk away from the ultrasonic transducer. At time $t_2$, the measured distance between the ultrasonic transducer and the disk is $D_2$, where $D_2 > D_0$. As shown in FIG. 5D, at time $t_3$ an trans-axial compressive force is being exerted on the ablation catheter tip resulting in a deformation of the disk both toward and away from the ultrasonic transducer. At time $t_3$, the measured distance between the ultrasonic transducer and the disk is $D_3$, where $D_3$ represents a displacement of the disk surface. In some embodiments, the ultrasonic transducer will receive a reflection of the transmitted ultrasonic impulse with a length that extends over a period of time greater than the initial impulse length—the change in time associated with the variance of the distance the ultrasonic impulse traveled. The displacement of the disk surface (and the associated variance in impulse length) being indicative of a force vector that is not exerted axial to the ablation catheter tip.

Figure 4D:
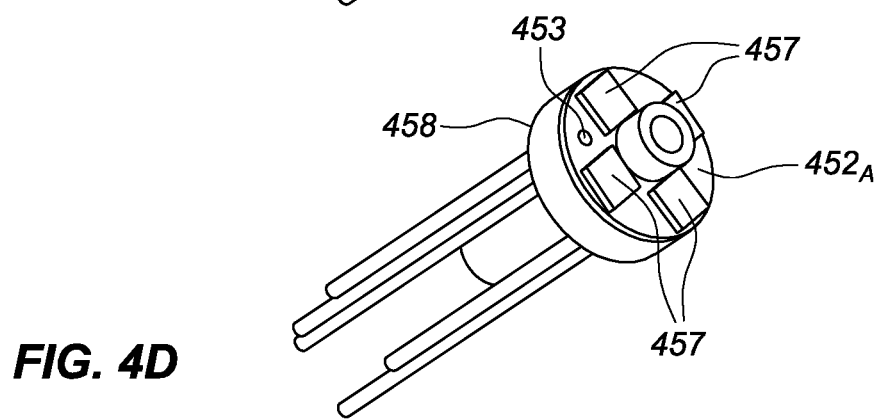
FIG. 4D is an isometric view of a partial ultrasonic transducer assembly, consistent with various aspects of the present disclosure.
Figure 6A:
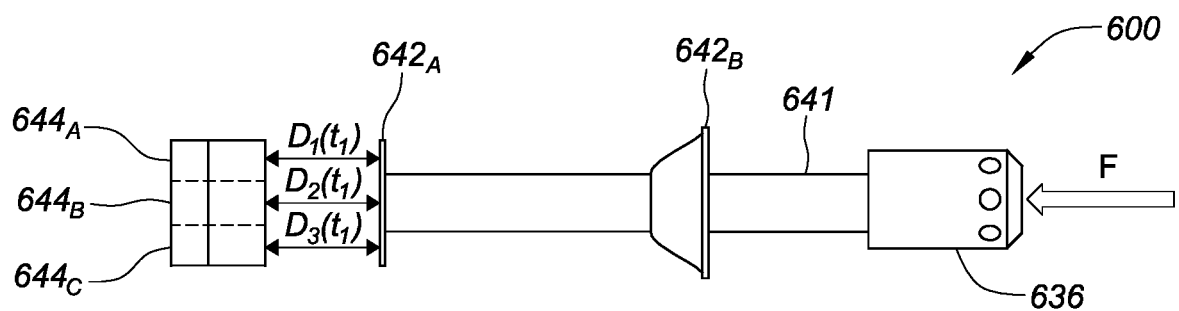
FIG. 6A is a side view of an ablation catheter tip subassembly, where the ablation catheter tip is under an axial compressive force, consistent with various aspects of the present disclosure.
Figure 6B:
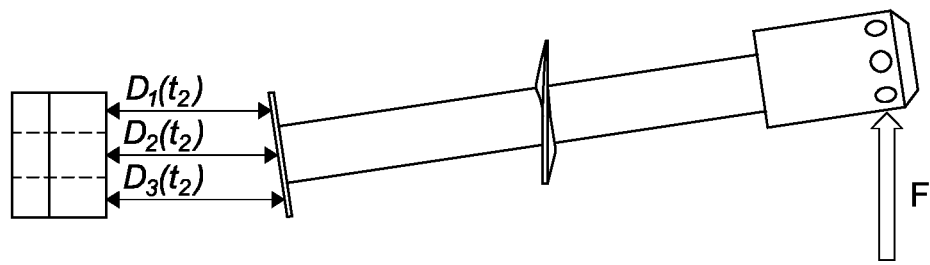
FIG. 6B is a side view of the ablation catheter tip subassembly of FIG. 6A, where the ablation catheter tip is under a trans-axial compressive force, consistent with various aspects of the present disclosure.
Figure 6C:
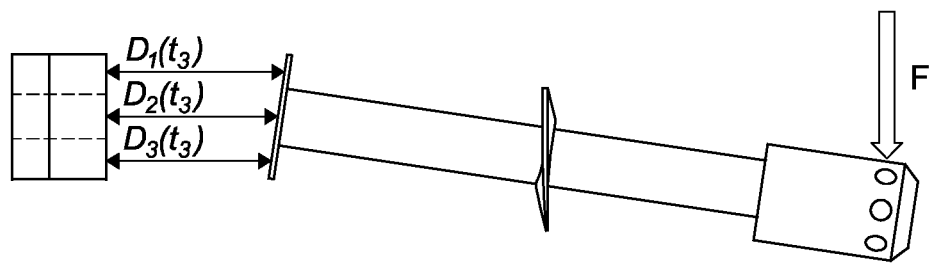
FIG. 6C is a side view of the ablation catheter tip subassembly of FIG. 6A, where an ablation catheter tip is under a trans-axial compressive force, consistent with various aspects of the present disclosure.

FIGS. 6A-6C show a simplified embodiment of an ablation catheter tip subassembly 600 where an ultrasonic probe including ultrasonic transducers 644$_{A-C}$ measures the displacement of disk 642$_A$ due to the deformation of disk 642$_B$, which is associated with a magnitude and vector of a force exerted on ablation catheter tip 636, and translated to the disk 642$_B$ by elongated shaft 641. FIG. 6A shows the ablation catheter tip subassembly with an axial compressive force exerted on the ablation catheter tip resulting in the longitudinal movement of the disk 642$_A$ toward the ultrasonic transducers. The measured distance between the ultrasonic transducers and the disk at time $t_1$ is $D_1(t_1) = D_2(t_1) = D_3(t_1)$, where $D_1(t_1) < D_0(t_0)$ (where $D_0(t_0)$ is indicative of the ablation catheter tip subassembly 600 at rest). As shown in FIG. 6B, at time $t_2$ a trans-axial compressive force is being exerted on the ablation catheter tip resulting in a deformation of the disks both toward and away from the ultrasonic transducers. The measured distances between the ultrasonic transducers and the disk 642$_A$ are $D_1(t_2)$, $D_2(t_2)$, $D_3(t_2)$, where $D_1(t_2) < D_0(t_0)$, $D_2(t_2) = D_1(t_1)$, and $D_3(t_2) > D_0(t_0)$, and thereby represent a non-perpendicular disk surface in front of the ultrasonic transducers. The non-perpendicular disk surface (and the associated varying distances measured by the ultrasonic transducers) are indicative of a force vector that is exerted trans-axial to the ablation catheter tip. Based on an analysis of the outputs of the ultrasonic transducers, the magnitude and vector of the trans-axial compressive force exerted on the ablation catheter tip may be determined. A similar analysis may be conducted for the system of FIG. 6C. In yet further embodiments of the present disclosure, the ultrasonic transducers are positioned circumferentially around the disk 642$_A$, without any of the ultrasonic transducers located at a central axis of elongated shaft 641 (as shown in FIG. 4D by way of example).

Embodiments of the present disclosure presented above include a single deformable disk. In such embodiments, optimization of a lateral stiffness associated with an axial stiffness, or an axial stiffness associated with a lateral stiffness may be achieved. Further aspects of the present disclosure are directed to embodiments including two deformable disks (as disclosed in more detail below). Dual deformable disk embodiments facilitate a desired trans-axial/axial compliance ratio.

In various more specific embodiments consistent with the present disclosure, an ablation catheter tip subassembly 600 may further include a third disk that in conjunction with disk 642$_B$ is deformed in association with a magnitude and vector of a force exerted on ablation catheter tip 636, and translated to the disks, including disk 642$_B$, by elongated shaft 641. In such an embodiment, both deformable disks are coupled to elongated shaft 641 at an inner diameter of the deformable disks and an external housing of deformable body 337 at an outer diameter of the deformable disks. In response to a force exerted on catheter tip 636, the two deformable disks are deformed and disk 642$_A$ is displaced relative to the ultrasonic transducers 644$_{A-C}$—the displacement associated with a magnitude and vector of a force exerted on ablation catheter tip 636, and translated to the two deformable disks by elongated shaft 641. A desired trans-axial/axial compliance ratio may be achieved in a dual deformable disk system. In response to a force at the catheter tip, the two disks are deformed. Dimensional aspects (e.g., thickness, diameter, and distance between the two deformable disks)

may be tuned in order to achieve the desired compliance ratio. Furthermore, the distance between the two deformable disks and the disk $642_A$ may also be tuned in order to amplify the lateral displacement the disk $642_A$ in response to a trans-axial force applied to a catheter tip.

Figure 7A:
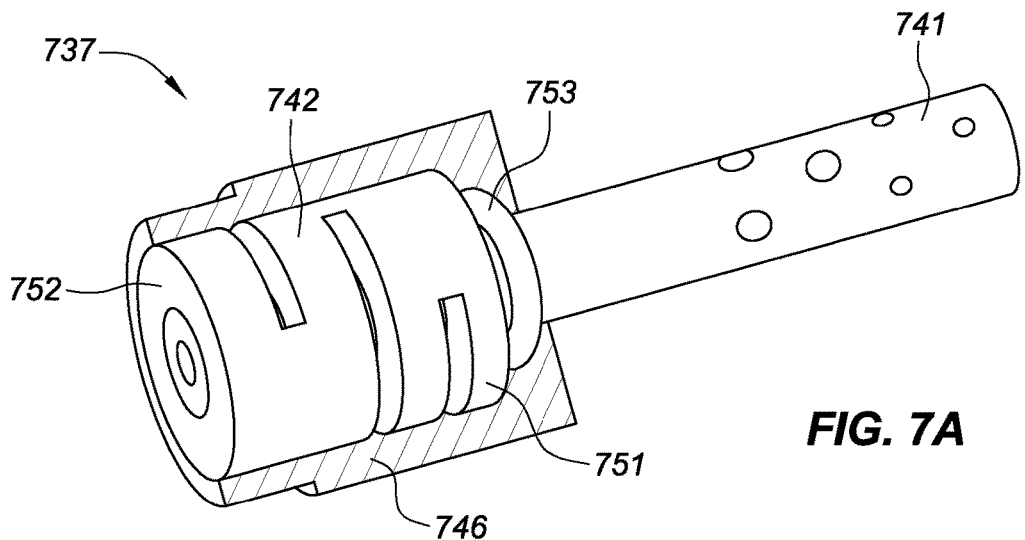
FIG. 7A is a partial cross-sectional side view of a deformable body, consistent with various aspects of the present disclosure.

FIG. 7A is a partial cross-sectional side view of a deformable body 737, consistent with various aspects of the present disclosure. As shown in FIG. 7A, the deformable body includes a housing 746 that contains an elastic structure 742 that is fixed to an elongated shaft 741 and the housing at a distal end 751 of the elastic structure. During use, O-ring 753 seals out an external environment. In response to a force being exerted at a distal end of the elongated shaft, the elastic structure deforms and moves a proximal face 752 of the elastic structure relative to a measurement device.

Figure 7B:
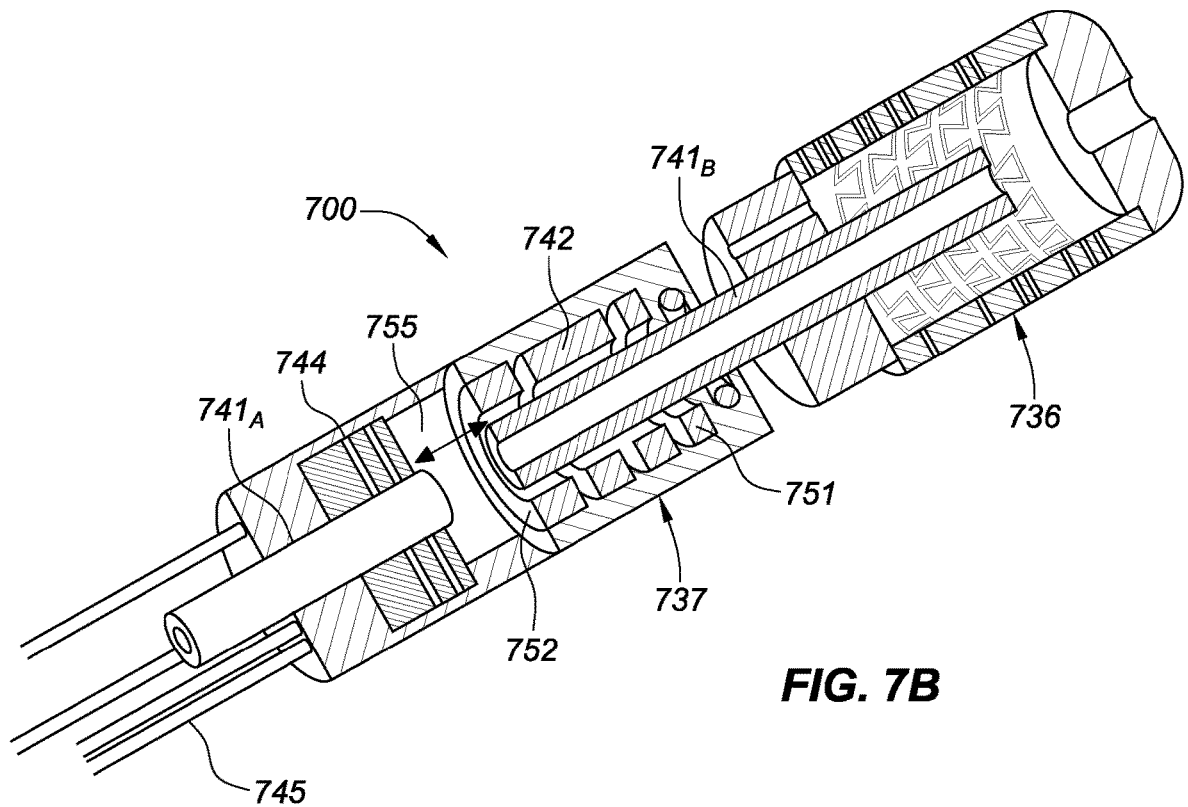
FIG. 7B is a cross-sectional side view of an ablation catheter tip subassembly including the deformable body of FIG. 7A, consistent with various aspects of the present disclosure.

FIG. 7B is a cross-sectional side view of an ablation catheter tip subassembly 700 including an ablation catheter tip 736 and deformable body 737 of FIG. 7A, consistent with various aspects of the present disclosure. The subassembly further includes elongated shaft portions $741_{A\text{-}B}$ that substantially extend the length of the subassembly and deliver (via an irrigant lumen within the elongated shaft) an irrigant fluid to the ablation catheter tip for cooling the blood pool during ablation therapies within a cardiac muscle. The second portion of the elongated shaft $741_B$ substantially supports the ablation catheter tip and transfers a force exerted on the ablation catheter tip into the deformable body. The force transferred by the second portion of elongated shaft $741_B$ to deformable body 737 is absorbed by the deformation of elastic structure 742.

During an ablation therapy of myocardial tissue within the heart, irrigant fluid flows through an irrigant lumen within elongated shaft $741_A$ which extends the length of the catheter shaft between a reservoir and an immersed zone (between the elastic structure 742 and the ultrasonic probe 744) which fills with the irrigant fluid before extending through an irrigant lumen within elongated shaft $741_B$ to ablation catheter tip 736 where the fluid exits the ablation catheter tip through one or more ports in the tip. The contact force exerted on the tissue by the ablation catheter tip is translated through elongated shaft $741_B$ and into elastic structure which deforms proportionally in response to the force exerted thereon. The deformation of the elastic structure changes the relative distance 755 between the elastic structure and the ultrasonic probe.

As discussed in more detail above, during ablation therapy, ultrasonic probe 744 measures the time-of-flight of an ultrasonic pulse, which varies based on the amount and directionality of the deformation of elastic structure 742. Based on the time-of-flight for the emitted ultrasonic pulse, back-end processing may then be utilized to calculate the distance between the elastic structure and the ultrasonic probe, and the associated force exerted upon the ablation catheter tip resulting in the deformation of the elastic structure. The ultrasonic probe 744 may be communicatively coupled to back-end processing circuitry via lead wires 745.

Figure 8A:
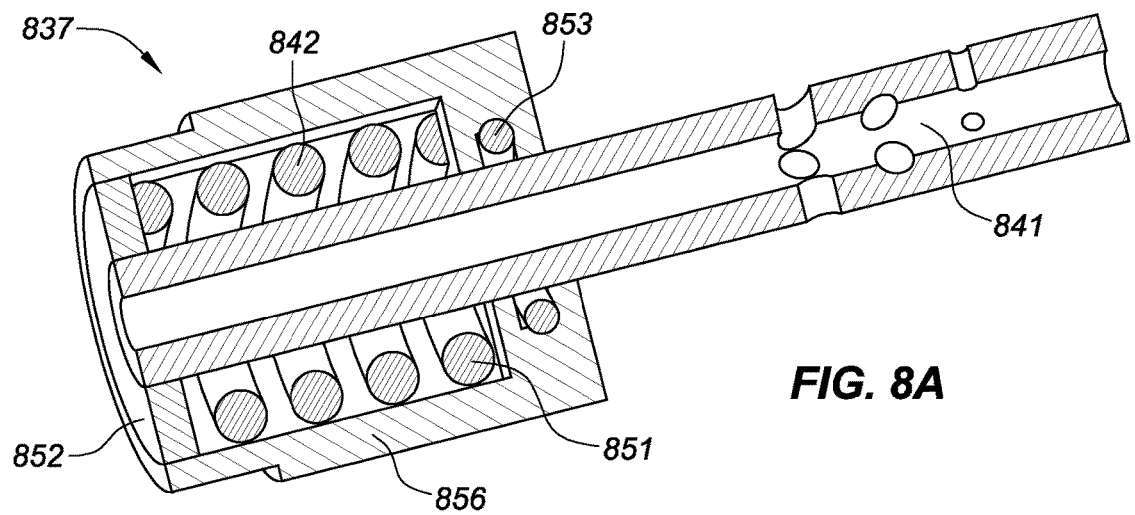
FIG. 8A is a cross-sectional side view of a deformable body, consistent with various aspects of the present disclosure.

FIG. 8A is a cross-sectional side view of a deformable body 837, consistent with various aspects of the present disclosure. As shown in FIG. 8A, the deformable body includes a housing 856 that houses spring 842 that is fixed to a proximal end of elongated shaft 841 and the housing at a distal end 851 of the spring. During use, O-ring 853 seals out an external environment. In response to a force being exerted at a distal end of the elongated shaft, the spring deforms and moves a proximal face 852 of the spring relative to a measurement device.

Figure 8B:
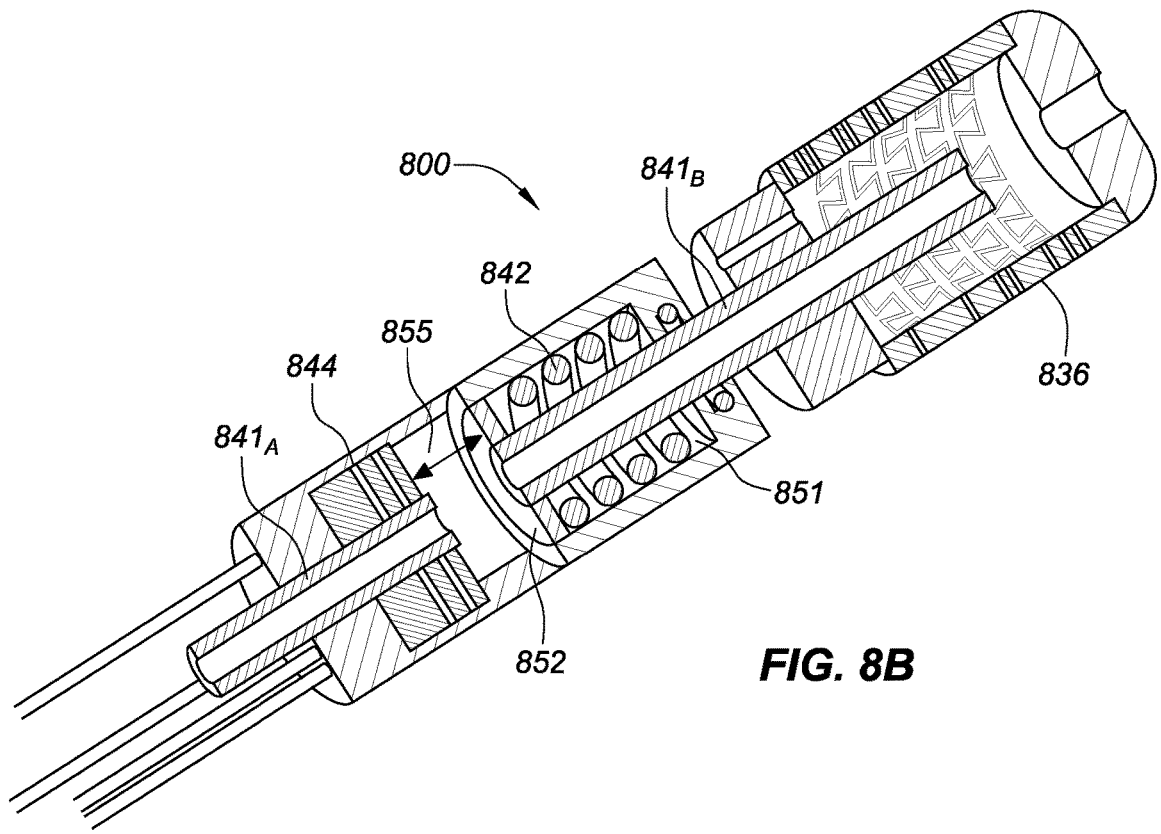
FIG. 8B is a cross-sectional side view of an ablation catheter tip subassembly including the deformable body of FIG. 8A, consistent with various aspects of the present disclosure.

FIG. 8B is a cross-sectional side view of an ablation catheter tip subassembly 800 including an ablation catheter tip 836 and spring 842 of FIG. 8A, consistent with various aspects of the present disclosure. The subassembly further includes elongated shaft portions $841_{A\text{-}B}$ that extend the length of the subassembly. The second portion of the elongated shaft $841_B$ transfers a force exerted on the ablation catheter tip to the spring which deforms proportionally in response thereto. The deformation of the spring changes the relative distance 855 between the elastic structure and an ultrasonic probe 844.

Figure 9:
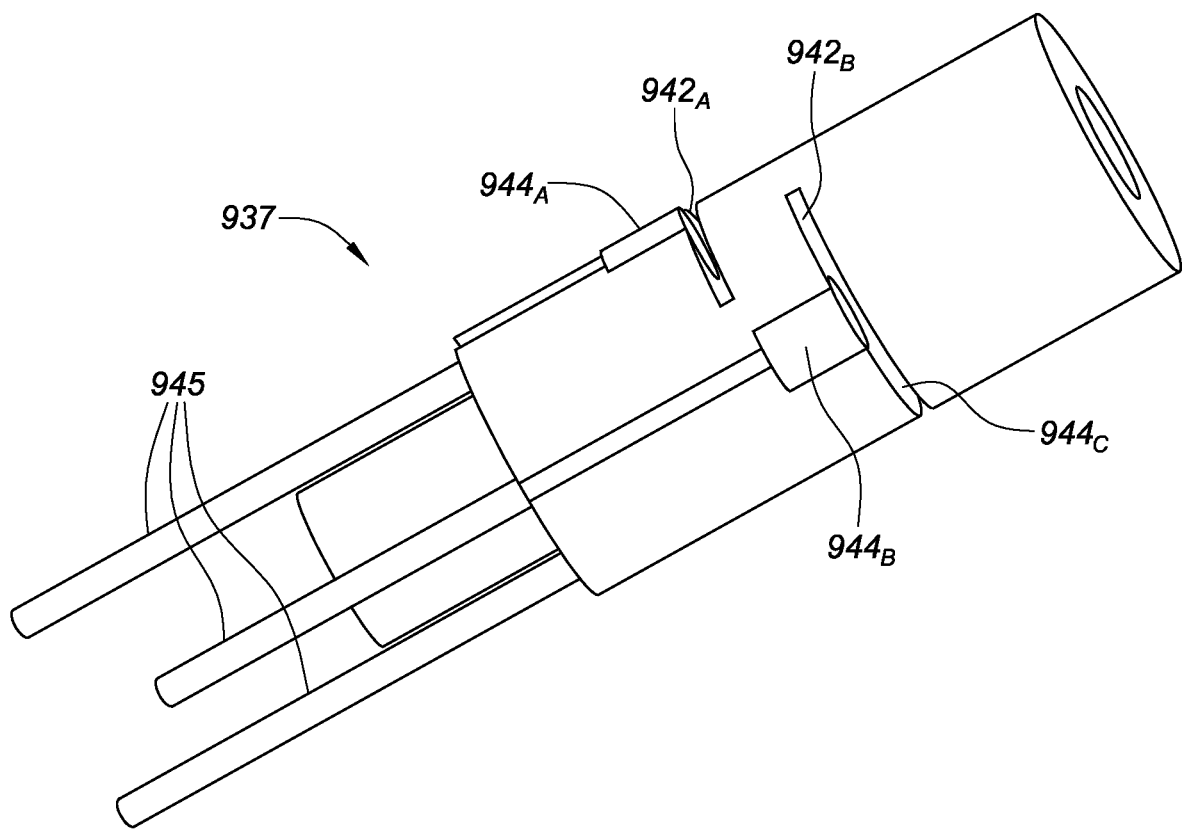
FIG. 9 is an isometric view of a deformable body, consistent with various aspects of the present disclosure.

FIG. 9 is an isometric view of a deformable body 937, consistent with various aspects of the present disclosure. In the present embodiment, each of the ultrasonic transducers $944_{A\text{-}C}$ measure indirectly the deformation of the corresponding elastic structures $942_{A\text{-}B}$, by measuring the distance variation between the ultrasonic transducers and the elastic structures spaced circumferentially along the deformable body. Where an axial force is exerted upon the deformable body, all of the elastic structures will similarly deform. Where a trans-axial force is exerted upon the deformable body, the trans-axial force induces a moment which causes an uneven deformation of the elastic structures. As a result, the data outputted from the ultrasonic probes through the lead wires 945 are indicative of both a magnitude and a vector of a force exerted upon the deformable body.

Force magnitudes and vectors associated with a given deformation of a deformable body may be determined and stored in a lookup table of a force sensing subsystem, which can be located at a proximal end of a catheter shaft, and external to the body. In other embodiments, the force sensing subsystem and other electronic circuitry can be located at a distal end of the catheter shaft. During an ablation therapy procedure, a measurement device may determine the deformation of the deformable body and send one or more signals to the force sensing subsystem indicative of the deformation of the deformable body measured by the measurement device. The force sensing subsystem, including various electronic circuitry, can process the various signals to derive the magnitude and vector of the force exerted on the catheter tip. Moreover, to achieve consistent force between an ablation catheter tip and tissue during an ablation procedure, the calculated force may be displayed to the clinician performing the procedure or otherwise communicated in a way that assists the clinician to maintain a substantially consistent exertion force on the tissue being ablated during both individual ablations and a series of ablations.

In one exemplary embodiment of the present disclosure, ultrasonic transducers measure the deformation of a deformable body relative to a fixed reference point. Transducer controller circuitry (e.g., a force sensing subsystem, or an ultrasonic transducer itself), communicatively coupled to the ultrasonic transducers, receives output signals from each of the ultrasonic transducers, and based on a time-of-flight between the ultrasonic transducer emitting the ultrasonic pulse and receiving a reflected ultrasonic pulse off of the deformable body, determines a distance between each respective ultrasonic transducer and the deformable body. Finally, based on an association between the deformation of the deformable body and the force exerted upon the catheter tip, the transducer controller circuitry estimates the force exerted on the catheter tip.

In more specific embodiments, transducer controller circuitry includes analog-to-digital converter circuitry, digital signal processing circuitry, and non-volatile memory circuitry. The analog-to-digital converter circuitry converts the analog output signals from the ultrasonic transducer into digital signals. The digital signal processing circuitry applies a time-of-flight distance algorithm to the digital signal to determine a distance between the deformable body and the ultrasonic transducer. Finally, the transducer controller circuitry accesses a lookup table stored in the non-volatile memory circuitry to associate the determined distance with the exerted force on the catheter tip, and to provide an indication of the exerted force on the catheter tip to a clinician operating the catheter.

In various embodiments, digital signal processing circuitry reduces a signal-to-noise ratio within an output signal of an ultrasonic transducer by applying one or more of the following signal processing solutions: parametric echo envelope models, a cross-correlation estimator, and a discrete extended Kalman filter.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Various modules or other circuits may be implemented to carry out one or more of the operations and activities described herein and/or shown in the figures. In these contexts, a "module" is a circuit that carries out one or more of these or related operations/activities (e.g., ablation controller circuitry, or a force sensing subsystem). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electrophysiological catheter system comprising: a catheter shaft; a catheter tip coupled to a distal end of the catheter shaft, and configured and arranged to conduct diagnostics or therapies on a cardiac muscle; an elongated shaft disposed within the catheter shaft and extending distally into the catheter tip; a deformable body disposed between the catheter shaft and the catheter tip and surrounding and coupled to the elongated shaft, and configured and arranged to deform in response to a force being primarily translated from the catheter tip, through the elongated shaft, to the deformable body, and where a magnitude and vector of the force on the catheter tip is discernible from the resulting deformation of the deformable body; and one or more measurement devices configured and arranged to measure the resulting deformation of the deformable body in response to the force on the catheter tip, and wherein the deformation of the deformable body is associated with the magnitude and vector of the force on the catheter tip.

2. The catheter system of claim 1, wherein the deformable body includes one or more flexible disks configured and arranged to absorb the force on the catheter tip by deforming relative to the one or more measurement devices, and wherein the resulting deformation of the one or more flexible disks is associated with the magnitude and vector of the force on the catheter tip.

3. The catheter system of claim 1, wherein the deformable body includes a housing, and one or more flexible disks, each of the flexible disks are coupled to the elongated shaft at an interior circumference of the flexible disk and to the housing along an outer circumference of the flexible disk, with the one or more flexible disks being spaced apart from one another along the length of the elongated shaft.

4. The catheter system of claim 3, wherein the deformable body is further configured and arranged to receive the force on the catheter tip, and translated through the elongated shaft to the deformable body; and a trans-axial/axial compliance ratio of the deformable body, in response to the force on the catheter tip, is less than 5, resulting in deformation of the deformable body that is independent of the vector of the force on the catheter tip.

5. The catheter system of claim 1, wherein the one or more measurement devices are ultrasonic transducers, each of the ultrasonic transducers configured and arranged to
transmit an ultrasonic pulse through fluid between the ultrasonic transducer and the deformable body,
receive a reflected ultrasonic pulse that is a time-delayed version of the ultrasonic pulse which has traveled through the fluid between the ultrasonic transducer and the deformable body, is reflected off of the deformable body, and back to the ultrasonic transducer, and
output a signal indicative of a distance between the ultrasonic transducer and the deformable body.

6. The catheter system of claim 5, wherein the elongated shaft defines an irrigant lumen, which is positioned within the catheter shaft and runs coaxial to a longitudinal axis of the catheter shaft, the irrigant lumen configured and arranged to deliver irrigant fluid to the catheter tip; and each of the ultrasonic transducers are further configured and arranged to output another signal in response to the ultrasonic transducer transmitting the ultrasonic pulse and not receiving the reflected ultrasonic pulse within a threshold time period, the other output signal indicative of an occlusion in the irrigant lumen within the elongated shaft preventing the flow of irrigant fluid to the catheter tip.

7. The catheter system of claim 5, wherein a variation in the output signal above a threshold is indicative of external contact with the catheter tip.

8. The catheter system of claim 1, wherein the one or more measurement devices are ultrasonic transducers, each of the ultrasonic transducers are configured and arranged to
transmit an ultrasonic pulse through fluid between the ultrasonic transducer and the deformable body, and
output a signal that is based at least in part on a deflection of the deformable body as indicated by the time-of-flight of the ultrasonic pulse.

9. The catheter system of claim 1, wherein the one or more measurement devices include at least three ultrasonic transducers configured and arranged to measure deformation of the deformable body at three or more different locations, and wherein an output of each of the ultrasonic transducers is indicative of the deformation of the deformable body, and a cumulative deformation of the deformable body, as measured by the at least three ultrasonic transducers, is indicative of the magnitude and the vector of the force on the catheter tip.

10. An electrophysiological catheter system comprising: a catheter shaft; a catheter tip coupled to a distal end of the catheter shaft, and configured and arranged to conduct diagnostics or therapies on tissue; an elongated shaft disposed within the catheter shaft and extending distally into the catheter tip; a deformable body disposed between the catheter shaft and the catheter tip and surrounding and coupled to the elongated shaft, and configured and arranged to deform in response to a force being primarily translated from the catheter tip, through the elongated shaft, to the deformable body, and where a magnitude and vector of the force on the catheter tip is discernible from the resulting deformation of the deformable body; a measurement device configured and arranged to measure the resulting deformation of the deformable body in response to the force on the catheter tip; and a force sensing subsystem configured and arranged to derive the magnitude and vector of the force on the catheter tip based on the measurements of the measurement device.

11. The catheter system of claim 10, wherein the measurement device includes at least three ultrasonic transducers; and the force sensing subsystem is communicatively coupled to the ultrasonic transducers, and configured and arranged to
receive analog output signals from each of the ultrasonic transducers indicative of the deformation of the deformable body,
determine a distance between each respective ultrasonic transducer and the deformable body based on a time-of-flight between the ultrasonic transducer emitting an ultrasonic pulse and receiving a reflected ultrasonic pulse, and
based on the deformation of the deformable body measured by each of the ultrasonic transducers, derive the magnitude and vector of the force on the catheter tip.

12. The catheter of claim 11, wherein the force sensing subsystem includes analog-to-digital converter circuitry, digital signal processing circuitry, and non-volatile memory circuitry, the analog-to-digital converter circuitry being configured and arranged to convert the analog output signals from each of the ultrasonic transducers into digital signals, the digital signal processing circuitry is configured and arranged to apply a time-of-flight distance algorithm to the digital signals to determine a distance between the deformable body and the ultrasonic transducers, and wherein the force sensing subsystem is further configured and arranged to access a lookup table stored in the non-volatile memory circuitry to associate the determined distances with the magnitude and the vector of the force on the catheter tip, and to provide an indication of the force on the catheter tip to a clinician operating the catheter.

13. The catheter of claim 12, wherein the digital signal processing circuitry is further configured and arranged to reduce a signal-to-noise ratio within one or more of the output signals by applying one or more of the following signal processing solutions: parametric echo envelope models, a cross-correlation estimator, and a discrete extended Kalman filter.

14. An electrophysiology ablation catheter system comprising: an ablation catheter tip configured and arranged to conduct ablation therapy on tissue; a catheter shaft; an elongated shaft disposed within the catheter shaft and extending distally into the catheter tip; a deformable body coupled to a proximal end of the ablation catheter tip and a distal end of the catheter shaft via the elongated shaft, the deformable body surrounding and coupled to the elongated shaft, the deformable body including one or more flexible disks that couple the ablation catheter tip to the catheter shaft, the deformable body configured and arranged to deform in response to a force being primarily translated from the catheter tip, through the elongated shaft, to the deformable body; and three or more ultrasonic transducers configured and arranged, in response to the force on the ablation catheter tip, to measure the resulting deformation at three or more points of the deformable body, and wherein the deformation of the deformable body, as measured by the three or more ultrasonic transducers, is indicative of both a magnitude and vector of the force on the ablation catheter tip.

15. The catheter system of claim 14, wherein each of the three or more ultrasonic transducers are configured and arranged to output an electrical signal indicative of the deformation of a portion of the deformable body, and wherein the three or more outputs are collectively indicative of both the magnitude and the vector of the force on the ablation catheter tip.

16. The catheter system of claim 14, wherein each of the ultrasonic transducers are configured and arranged to
   transmit an ultrasonic pulse through fluid between the ultrasonic transducer and the deformable body,
   receive a reflection of the transmitted pulse at a later time indicative of a distance between the ultrasonic transducer and the deformable body, and
   output a signal indicative of the distance between the ultrasonic transducer and the deformable body.

17. The catheter system of claim 14, wherein the ablation catheter tip is further configured and arranged to transfer a resultant force exerted on the catheter tip to the deformable body during an ablation therapy, where the resultant force is a vector sum of one or more forces, including the force, being exerted on the ablation catheter tip by myocardial tissue within a cardiac muscle, and the deformation of the deformable body, in response to the resultant force, is indicative of both a magnitude and a vector of the resultant force.

18. The catheter system of claim 14, further including a force sensing subsystem communicatively coupled to the ultrasonic transducers, and configured and arranged to
   receive output signals from each of the ultrasonic transducers,
   determine a distance between each ultrasonic transducer and the deformable body based on a time-of-flight between the ultrasonic transducer emitting an ultrasonic pulse and receiving the reflected ultrasonic pulse, and
   based on an association between the deformation of the deformable body and the force upon the ablation catheter tip, determine both the magnitude and vector of the force on the ablation catheter tip.

19. The catheter system of claim 18, wherein the force sensing subsystem includes analog-to-digital converter circuitry, digital signal processing circuitry, and non-volatile memory circuitry, the analog-to-digital converter circuitry configured and arranged to convert an analog output signals from each of the ultrasonic transducers into digital signals, the digital signal processing circuitry configured and arranged to apply a time-of-flight distance algorithm to the digital signals to determine the distance between the deformable body and each of the ultrasonic transducers, and wherein the force sensing subsystem is further configured and arranged to access a lookup table stored in the non-volatile memory circuitry to associate the determined distances with the force on the ablation catheter tip, and to provide an indication of the force on the catheter tip to a clinician operating the catheter.

* * * * *